United States Patent
Caduff et al.

(10) Patent No.: US 9,549,695 B2
(45) Date of Patent: Jan. 24, 2017

(54) OPTICAL DETERMINATION OF BLOOD PERFUSION AND SIMILAR PARAMETERS

(75) Inventors: Andreas Caduff, Schmerikon (CH); Hans-Joachim Krebs, Lachen (CH); Mark Stuart Talary, Zurich (CH); Pavel Zakharov, Zurich (CH)

(73) Assignee: BIOVOTION AG, Zurich (CH)

( * ) Notice: Subject to any disclaimer, the term of this patent is extended or adjusted under 35 U.S.C. 154(b) by 862 days.

(21) Appl. No.: 13/581,191

(22) PCT Filed: Feb. 26, 2010

(86) PCT No.: PCT/CH2010/000049
§ 371 (c)(1),
(2), (4) Date: Nov. 5, 2012

(87) PCT Pub. No.: WO2011/103690
PCT Pub. Date: Sep. 1, 2011

(65) Prior Publication Data
US 2013/0053654 A1 Feb. 28, 2013

(51) Int. Cl.
*A61B 5/1455* (2006.01)
*A61B 5/01* (2006.01)
*A61B 5/1491* (2006.01)
*A61B 5/00* (2006.01)

(52) U.S. Cl.
CPC ........... *A61B 5/1455* (2013.01); *A61B 5/1491* (2013.01); *A61B 5/14552* (2013.01); *A61B 5/441* (2013.01); *A61B 5/01* (2013.01)

(58) Field of Classification Search
CPC ............ A61B 5/14551; A61B 5/14552; A61B 5/6826; A61B 5/6838; A61B 5/1495
See application file for complete search history.

(56) References Cited

U.S. PATENT DOCUMENTS

| 3,796,213 A | 3/1974 | Stephens |
| 4,086,915 A | 5/1978 | Kofsky et al. |
| 4,867,557 A | 9/1989 | Takatani et al. |

(Continued)

FOREIGN PATENT DOCUMENTS

| CA | 2 637 855 A1 | 12/1996 |
| DE | 19720300 A1 | 12/1997 |

(Continued)

OTHER PUBLICATIONS

International Preliminary Report on Patentability dated Aug. 28, 2012 for Application No. PCT/CH2010/000049.

(Continued)

*Primary Examiner* — Tse Chen
*Assistant Examiner* — Yoojin Lee
(74) *Attorney, Agent, or Firm* — Ladas & Parry LLP

(57) ABSTRACT

A parameter affecting the absorptivity or the concentration of blood in tissue is measured using a semiconductor light source (7) and a light detector (8). The semiconductor light source (7) is operated at several operating conditions, at which it has different temperatures and therefore different emission spectra. In particular, the operating conditions correspond to different time intervals after switching the light source (7) on, while the light source (7) has not yet reached thermal equilibrium. This allows to perform a spectroscopic measurement using one light source only, which increases accuracy and reduces device cost.

18 Claims, 8 Drawing Sheets

(56) References Cited

U.S. PATENT DOCUMENTS

| | | | |
|---|---|---|---|
| 4,869,253 | A | 9/1989 | Craig, Jr. et al. |
| 5,167,230 | A | 12/1992 | Chance |
| 5,277,181 | A | 1/1994 | Mendelson et al. |
| 5,372,136 | A | 12/1994 | Steuer et al. |
| 5,758,644 | A | 6/1998 | Diab et al. |
| 6,070,092 | A | 5/2000 | Kazama et al. |
| 6,526,298 | B1 * | 2/2003 | Khalil et al. ............ 600/310 |
| 6,631,288 | B1 | 10/2003 | Bain et al. |
| 6,802,812 | B1 | 10/2004 | Walker et al. |
| 6,862,542 | B2 | 3/2005 | Lockhart et al. |
| 6,928,311 | B1 | 8/2005 | Pawluczyk et al. |
| 7,030,359 | B2 | 4/2006 | Romhild |
| 7,043,287 | B1 * | 5/2006 | Khalil et al. ............ 600/310 |
| 2004/0065158 | A1 | 4/2004 | Schrepfer et al. |
| 2005/0256384 | A1 | 11/2005 | Walker et al. |
| 2006/0211922 | A1 | 9/2006 | Al-Ali et al. |
| 2007/0282180 | A1 | 12/2007 | Caduff et al. |
| 2009/0312615 | A1 | 12/2009 | Caduff et al. |
| 2012/0101351 | A1 | 4/2012 | Caduff et al. |

FOREIGN PATENT DOCUMENTS

| | | |
|---|---|---|
| EP | 0 832 421 B1 | 8/2002 |
| WO | 99/28971 A1 | 6/1999 |

OTHER PUBLICATIONS

Written Opinion of the International Searching Authority and International Search Report dated Nov. 26, 2010 for Application No. PCT/CH2010/000049.

Espacenet English abstract of DE 19720300 A1 and machine translation.

Espacenet English abstract of WO 99/28971 A1 and machine translation.

Diffey, B.L., et al., "A portable instrument for quantifying erythema induced by ultraviolet radiation", British Journal of Dermatology (1984) 111, pp. 663-672.

Berardesca, Enzo, et al., "Bioengineering of the Skin: Cutaneous Blood Flow and Erythema", CRC Press, 1995, pp. 231-240.

Liu, Hanli, et al., "Determination of optical properties and blood oxygenation in tissue using continuous NIR light", Phys. Med. Biol. 40 (1995), pp. 1983-1993.

Nijboer, J.A., et al, "Photoelectric plethysymography-some fundamental aspects of the reflection and transmission method", Clin. Phys. Physiol. Meas., 1981, vol. 2, No. 3, pp. 205-215.

Feather, J.W., et al., "A portable scanning reflectance spectrophotometer using visible wavelengths for the rapid measurement of skin pigments", Phys. Med. Biol., 1989, vol. 34, No. 7, pp. 807-820.

Serup, Jorgen, et al., "Handbook of Non-Invasive Methods and the Skin-Second Edition", CRC Taylor & Francis Group, 2006, Table of Contents and pp. 665-671.

Osawa, Masahiko, et al., "A portable diffuse reflectance spectrophotometer for rapid and automatic measurement of tissue", Meas. Sci. Technol. 4, (1993), pp. 668-676.

Nitzan, Meir, et al., "Three-wavelength technique for the measurement of oxygen saturation in arterial blood and in venous blood", Journal of Biomedical Optics, vol. 14(2), (Mar./Apr. 2009), pp. 024046-1-024046-5.

Sinichkin, Yu.P, et al., Reflectance and Fluorescence Spectroscopy of Human Sin in vivo with English translation, pp. 1-52.

Zakharov, P., et al., "A wearable diffuse reflectance sensor for continuous monitoring of cutaneuos blood content", Physics in Medicine and Biology 54, (2009), pp. 5301-5320.

\* cited by examiner

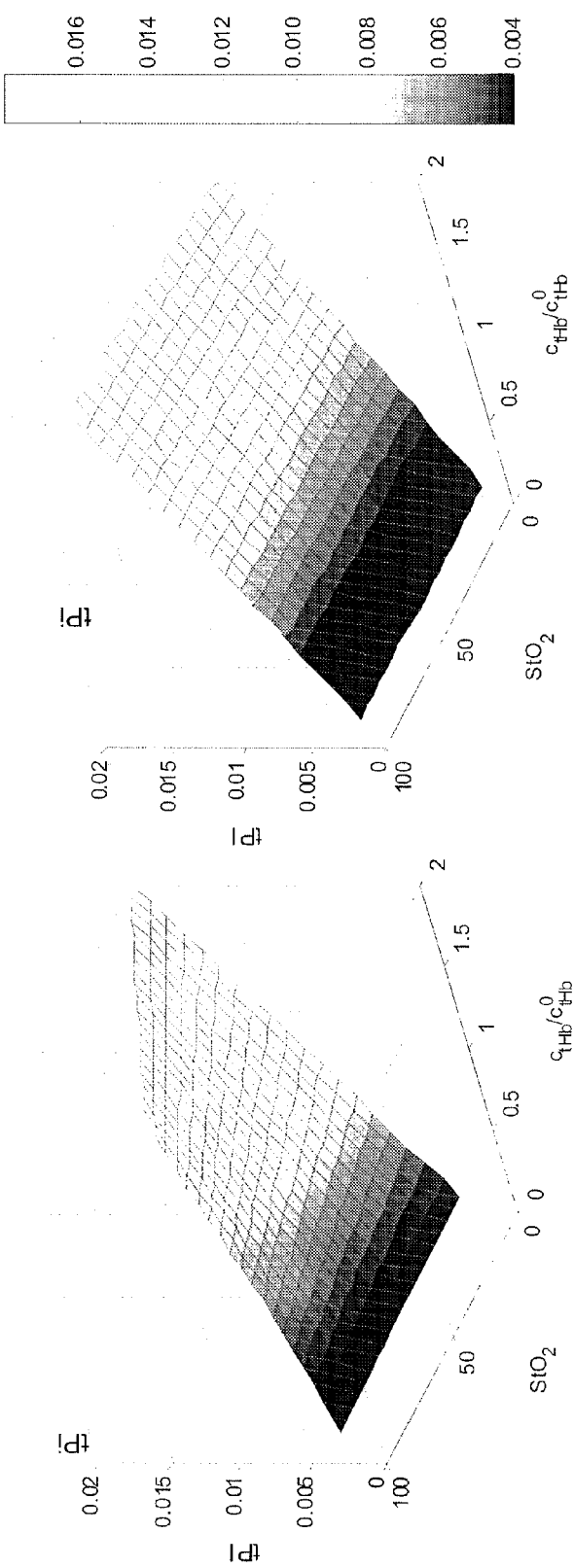

| Signal | Coefficient | r-value | p-value |
|---|---|---|---|
| $A(\lambda_1)$ | -2.9626e+004 | -3.4454e+001 | $<10^{-5}$ |
| $A(\lambda_3)$ | 2.9926e+004 | 3.4434e+001 | $<10^{-5}$ |
| $A(\lambda_2)$ | -1.5290e+001 | -3.3219e+001 | $<10^{-5}$ |
| -log(monitoring diode) | -4.2590e+002 | -1.0319e+001 | $<10^{-5}$ |
| Skin temperature | 1.2944e+001 | 1.2827e+001 | $<10^{-5}$ |
| Baseline | -4.4726e+002 | -1.1856e+001 | $<10^{-5}$ |
| $R^2$ | | 0.680 | |
| RMS error | | 7.14 % | |

OPTICAL DETERMINATION OF BLOOD PERFUSION AND SIMILAR PARAMETERS

TECHNICAL FIELD

The invention relates to a method for the in-vivo measurement of at least one physiological parameter of tissue by means of a semiconductor light source and of a light detector. In particular, the invention relates to a method for measuring a parameter that affects concentration of blood constituents, in particular different forms of hemoglobin. The invention also relates to a device of this type.

BACKGROUND ART

It has been known to measure blood content and also blood oxygenation from the absorption spectrum of skin measured in reflection or transmission. A corresponding methods are extensively covered e.g. in corresponding collections Berardesca 1995, Serup 2006 (see section "further references" at the end of this text) and the references therein.

For example, it has been known to measure blood oxygenation by measuring tissue spectrum with a broad band source [Osawa 1993, Feather 1989, Liu 1995] or at several wavelengths in the visible and infrared spectral range [Nitzan 2009, Diffey 1984, Sinichkin 2002].

More details on a conventional spectroscopic approach for measuring blood content are given in the section "conventional approach" below.

DISCLOSURE OF THE INVENTION

It is a general object of the present invention to provide a method and device that allow accurate spectral measurements of the type above.

This object is achieved by the method and device according to the independent claims.

Accordingly, the method is based on using a device having a semiconductor light source and a light detector. The method comprises the following steps:

a) placing said light source and said light detector such that said light detector measures an amount of light transmitted from said light source through said tissue, b) operating said light source under a first condition where it has a first temperature, and determining a first attenuation signal by means of said light detector, c) operating said light source under a second condition where it has a second temperature different from the first temperature, and determining a second attenuation signal by means of said light detector, d) determining said parameter using said first signal and said second attenuation signal.

In other words, the optical attenuation of light in the tissue is measured using a light source that is operated under at least two operating conditions. Under the different operating conditions, the semiconductor light source has different temperatures. Since the wavelength of a semiconductor light source depends on temperature, the two or more attenuation signals correspond to different optical wavelengths or spectra. Hence, the present procedure allows to measure the optical attenuation of the tissue at different wavelengths, which allows to carry out a spectroscopic measurement. However, since both measurements are carried out with the same light source and detector, they share the same interaction volume with the tissue, in contrast to conventional methods where several light sources of different wavelengths are used, which gives rise to errors due to differing volumes of interaction. Also, since the device can carry out a measurement with only one light source, it can be cheaper. (Albeit a device according to the invention can also use several light sources for carrying out several separate measurements.)

The desired parameter can e.g. be any parameter depending on tissue blood perfusion, such as the blood concentration or blood volume in the tissue, or it can be a parameter depending on blood oxygenation, or it can be a value derived from such parameters, such as a heart beat rate. It can be calculated from the measured attenuation signals by means of a theoretical, empirical or semi-empirical model that links the attenuation signals to the parameters.

In an advantageous model, the parameter is determined using the attenuation signals and calibration data, wherein the calibration data was obtained in a calibration procedure. Such a calibration procedure typically comprises the following steps:

Performing a series of calibration measurements for different states of said tissue. At least some of these states should correspond to different values of the parameter to be measured. For each calibration measurement, the attenuation signals are recorded by means of the light detector and the value of the parameter is recorded by means of a reference method. The reference method can be any method capable of measuring the parameter, such as a conventional method.

Using multiple regression for determining the calibration data using then the recorded attenuation signals as independent variables and the recorded values of the parameter as dependent variable.

To create different operating conditions of the light source, which correspond to different temperatures within the light source, the light source can e.g. be provided with an adjustable heater. Advantageously, though, the current through the light source is varied in order to create the different operating conditions.

In a most simple embodiment, the method comprises the step of switching the current through the light source from a first level to a second level, with the two levels being different. The first level can e.g. correspond to zero current, while the second level can correspond to the operating current for the light source. At least part of the attenuation signals are determined at different times after switching the current but while the light source has not yet reached thermal equilibrium. In other words, the measurements are carried out while the light source is heating up. For many light sources, the best time to carry out at least part of the measurements is within 1 second from switching the current because the temperature changes rapidly during this time.

In addition, for many applications; the measurements of tissue microcirculation should be performed within a fraction of a single heart beat. For LEDs sufficient temperature change can be achieved within 100 milliseconds from switching on the current which is within the typical period of heart beat of around 1 second. Therefore, advantageously the measurements are carried out within 100 milliseconds from switching the current.

The present method is especially suited for measuring blood perfusion or blood oxygenation.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 12 shows tPI vs. $StO_2$ and tHb concentration for type B LED, FIG. 13 shows tPI vs. $StO_2$ and tHb concentration for type A LED.

MODES FOR CARRYING OUT THE INVENTION

Definitions

Figure 1:
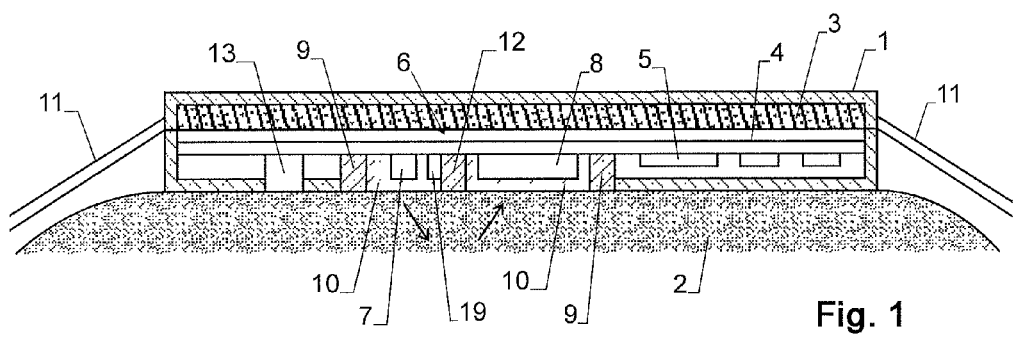
FIG. 1 shows a sectional view of an embodiment of a device.

"Blood perfusion" designates any measure that describes the amount of blood in a given region of body tissue. It may e.g. be described by molar hemoglobin concentration per tissue volume.

oxyHb designates oxygenated hemoglobin, i.e. hemoglobin with an oxygen attached, the corresponding concentration defined as $c_{oxyHb}$ rHb designates reduced hemoglobin, i.e. hemoglobin without oxygen, the corresponding concentration is $c_{rHb}$ Hb and tHb designate hemoglobin of any form, i.e. the total amount of hemoglobin, the corresponding concentration is $c_{tHb}=c_{oxyHb}+c_{rHb}$.

$StO_2$, or tissue oxygenation, is the percentage of oxygenated hemoglobin in the total hemoglobin mass, including venous, arterial and capillary blood. It is defined in the following way $StO_2=c_{oxyHb}/c_{tHb}*100\%$ The arterial blood oxygenation $SaO_2$ is typically around 95-97%, while $StO_2$ in the skin is around 30-40%.

Conventional Spectroscopic Approach:

Below we describe the spectroscopic approach for measuring blood perfusion (blood concentration) using measurements with two probing wavelengths.

The absorption of light in an absorbing compound having a given concentration c is given by the exponential Beer-Lambert law $$I=I_0 \cdot \exp(-cl\epsilon) \quad (1)$$

with $I_0$ being the original intensity prior to absorption, l the length traversed by the light, c the concentration of the absorbing compound, $\epsilon$ its absorptivity, and I the exiting intensity.

The attenuation A is given by $$A = -\ln\frac{I}{I_0} = cl\varepsilon \quad (2)$$

Hence, the concentration can be calculated from the attenuation by $$c = \frac{A}{l\varepsilon} \quad (3)$$

When the attenuation is not only defined by the single substance of interest (hemoglobin Hb), but is also due to other absorbers, scattering, loss of intensity due the Fresnel reflections on the interfaces etc., which we will call background attenuation $A_{bk}$, total attenuation is the sum of both $$A=A_{Hb}+A_{bk}=cl\epsilon_{Hb}+A_{bk} \quad (4)$$

If $A_{bk}$ can be assumed to be stable in time, while concentration c is evolving, the concentration change $\Delta c$ can be extracted from the difference $\Delta A$ in attenuation with $$\Delta c = \frac{\Delta A}{l\varepsilon} \quad (6)$$

However in real-life conditions, if the sample under study is composed of a complex set of various compounds, background attenuation might evolve as well and thus attenuation change in time can not be attributed solely to the substance of interest (hemoglobin).

Since the absorptivity $\epsilon$ is the wavelength dependent, Eq. (4) becomes $$A(\lambda)=cl\epsilon_{Hb}(\lambda)+A_{bk}(\lambda) \quad (7)$$

In Eq. (7) we assumed that the path length l does not depend on the wavelength $\lambda$, but the background attenuation $A_{bk}$ does. One can perform measurements on a set of several wavelengths in order to combine the information and extract concentration of the substance of interest. For example, if the wavelengths $\lambda_1$ and $\lambda_2$ are chosen in such a way that the difference in light attenuation by the hemoglobin is large, i.e.

$$\epsilon_{Hb}(\lambda_1) \gg \epsilon_{Hb}(\lambda_2), \tag{8}$$

while the attenuation difference of the background is small $$A_{bk}(\lambda_1) \approx A_{bk}(\lambda_2), \tag{9}$$

we obtain $$A(\lambda_1)-A(\lambda_2)=A_{Hb}(\lambda_1)-A_{Hb}(\lambda_2)+A_{bk}(\lambda_1)-A_{bk}(\lambda_2) \approx -cl[\epsilon_{Hb}(\lambda_1)-\epsilon_{Hb}(\lambda_2)] \tag{10}$$

In this case $\lambda_1$ is often called the signal wavelength, since it has the highest sensitivity to the compound concentration, while $\lambda_2$ is called the reference, since it serves to characterize the background attenuation.

The difference $A(\lambda_1)-A(\lambda_2)$ is called the perfusion index PI, i.e.

$$PI = A(\lambda_1) - A(\lambda_2) \tag{11}$$

In the conventional multi-source technique of the diffuse reflectance spectroscopy, the wavelengths of 568 and 798 nm have been chosen in the previous studies for the characterization of blood content in the skin (Zakharov, et. al., "A wearable diffuse reflectance sensor for continuous monitoring of cutaneous blood content". P. Zakharov, M. S. Talary and A. Caduff, Phys Med Biol. 2009, 54(17): 5301-20). This set-up has demonstrated high sensitivity and specificity to blood content. However, such an arrangement requires two separate light-emitting diodes (LED) of significantly different wavelengths. A two-LEDs-system has the disadvantage of being technologically more complex than a single-LED system and one cannot be sure that both wavelengths are probing the same tissue volume. The disadvantage of the high wavelength separation of the signal and reference wavelengths is that the differences in the background attenuation can become significant and thus its impact can not be completely eliminated from the signal. Another problem is the more pronounced difference in the light path length in the tissue $l(\lambda_1) \neq l(\lambda_2)$ due to the different absorption efficiency in the tissue of the different wavelengths.

For this reason, the present invention uses a different solution that can operate on a single light source. This approach is described in the following.

The Device:

FIG. 1 shows a device having a housing 1 to be attached to a body part 2, such as an arm or a leg, e.g. by means of a wristband 11. The device contains a power supply 3 as well as a circuit board 4 carrying various circuitry 5 and an optical sensor 6. Optical sensor 6 comprises at least one monolithic semiconductor light source 7 as well as a light detector 8, e.g. arranged in a common enclosure 9 and cast into resin 10 transparent for the wavelengths emitted by light source 7. Optical sensor 6 is arranged at the side of housing 1 that faces body part 2, such that light emitted by light source 7 enters the tissue of body part 2, where it is transmitted and scattered. Part of the light from light source 7 propagates through the tissue to be diffusively reflected back into optical sensor 6, where it is detected by optical detector 8. A non-transparent barrier 12 between light source 7 and light detector 8 prevents light of light source 7 from arriving at light detector 8 without having passed through the tissue of body part 2.

The optical sensor can e.g. be of the design described in U.S. Pat. No. 7,030,359.

The device further comprises a temperature sensor 13 that is in thermal contact with body part 2 and adapted to measure the skin temperature $T_S$ of the body part, which also defines the equilibration temperature of the LEDs.

Figure 2:
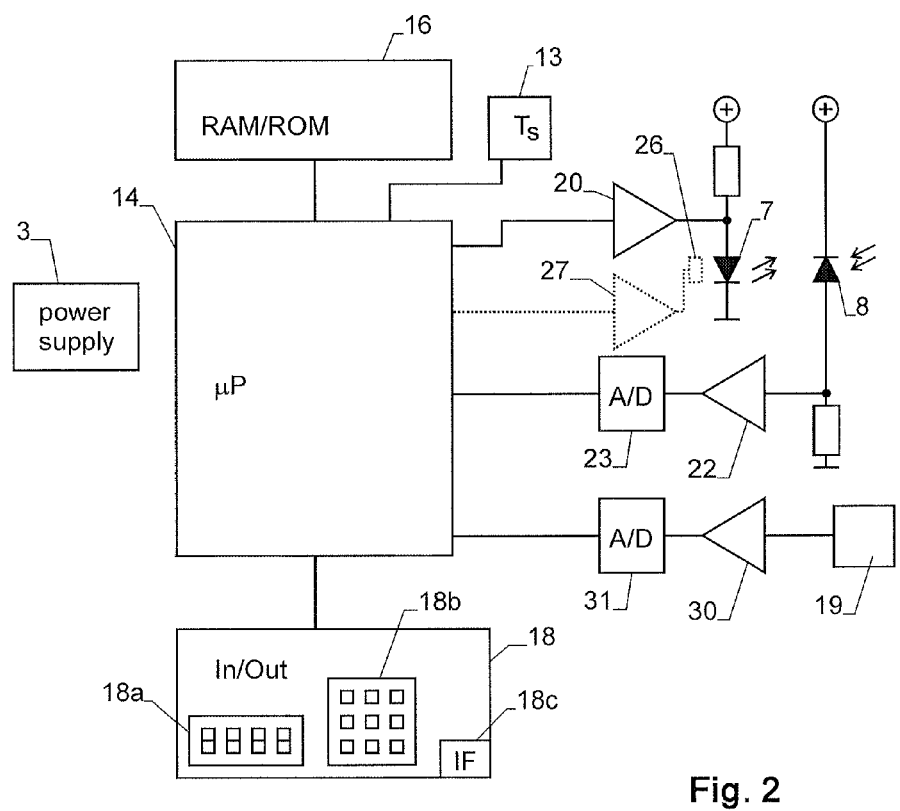
FIG. 2 shows a block circuit diagram of the device of FIG. 1.

A circuit block diagram of the device of FIG. 1 is shown in FIG. 2. The device comprises a control unit 14, such as a suitably programmed microprocessor connected to a memory 16 and an input/output device 18. Memory 16 holds program code and data for control unit 14. Input/output device 18 contains e.g. a display 18a as well as one or more user-operatable controls, such as buttons 18b, and/or interface circuitry 18c for connecting the device to a remote computer.

As can also be seen in FIG. 2, control unit 14 is connected to light source 7 via a driver unit 20, such as an amplifier, thus that control unit 14 is able to vary the current through light source 7, e.g. for switching light source 7 on and off.

The signal from light detector 8, which may e.g. be a PIN-diode, is fed through an amplifier 22 and A/D-converter 23 to control unit 14.

The elements shown in circuit block diagram 2 are powered by power supply 3.

In the following description, reference is made to two types of light sources. A first type of light source, called "type A light source", is a LED light source with a steady state mean wavelength of around 578 nm, such as AlInGaP-based chip produced by EPIGAP Optoelektronik GmbH (Germany). This type of LED is optimized for tHb concentration measurements.

A second type of light source, called "type B light source", is a LED light source with a steady state mean wavelength of around 571 nm made with the same technology, also produced by EPIGAP Optoelektronik GmbH (Germany). It must be noted, though, that the invention is not limited to these two types of light sources. Light source 7 can also be any other type of LED, semiconductor laser diode (LD), superluminescent diode (SLD) any other type of semiconductor light source. This type of LED is optimized for the tissue oxygenation measurements.

Most of the measurements on these LEDs were carried out in "cold" and "hot" state. In the cold state, right after being switched on, type A LED had a mean wavelength of 577.52 nm, and in hot state 578.07 nm, corresponding an estimated temperature difference $\Delta T$ of 6.88° C. between cold and hot state. Type B LED had a mean wavelength of 570.31 nm in cold state and of 571.18 nm in hot state, corresponding to $\Delta T=10.23$.

Light detector 8 can be any suitable light sensor being sufficiently sensitive at the spectrum emitted by light source 7 and sufficiently fast for the described purpose.

The device may further be equipped with a monitoring unit 19 adapted to directly determine the light intensity emitted by light source 7. Monitoring unit 19 can be a light detector arranged to directly receive light from light source 7, i.e. to receive light from light source 7 that has not passed via body part 2. Alternatively, monitoring unit 19 may be a temperature sensor in thermal contact with light source 7. With any such monitoring unit 19, changes of the light intensity emitted by light source 7 can be detected, either by direct measurement (if monitoring unit 19 is a light detector) or by means of a conversion table or conversion circuitry (if monitoring unit 19 is a temperature sensor). Using a temperature sensor instead of a light source as monitoring unit 19 is possible because changes in temperature are the main factor affecting the intensity emitted by light source 7.

The signal from monitoring unit 19 is fed through an amplifier 30 and A/D-converter 31 to control unit 14.

Mode of Operation:

In a first embodiment, control unit 14 repetitively switches light source 7 on and off, leaving sufficient time between on-states for an at least partial or substantially complete cooling of light source 7, while the duration of an on-state is sufficient to heat up the light source at least partially or, advantageously, until it reaches thermal equilibrium. When current is switched on, light source 7 starts to emit light while its temperature increases. This, in turn, leads to a shift of the spectrum of the light emitted by light source 7 to longer wavelengths, thus that measurements at different wavelengths can be carried out while light source 7 is heating up.

While light source 7 is heating up, control unit 14 records the intensity signal I from light detector 8 at least at two different times, advantageously at more than two different times, which allows to carry out a several measurements corresponding to different emission spectra of light source 7.

In a second embodiment, instead of switching light source 7 on and off, it may also be operated with at least two different non-zero currents. Since the currents give rise to different temperatures in light source 7, this again allows to perform measurements with different emission spectra. The two or more different currents can be generated by interposing a D/A-converter between control unit 14 and driver 20. Alternatively, the currents can be generated using pulse width modulation, i.e. by pulsing the current with a pulse rate much faster than the thermal inertia of light source 7.

Alternatively, in a third embodiment, a heater 26 could be provided in thermal contact with light source 7 and driven by a driver 27, which allows to adjust the temperature of light source 7 without varying the current through light source 7.

If the device is equipped with a monitoring unit 19 as described above, a factor $\alpha$ for the intensity $I_0$ emitted by light source 7 is generated from the signal of monitoring unit 19. Factor $\alpha$ accounts for variations in emitted baseline intensity, which can be caused e.g. by long-term effects of light-source aging or short-term variations caused by the changes of the baseline source temperature.

In practice, this requires the signal from light detector 8 to be scaled, in particular divided, by the factor $\alpha$ in order to correctly relate the measured intensity signal I to the emitted intensity $I_0$ and, correspondingly, attenuation A.

In the following further description, unless noted otherwise, it is assumed that the device is operated according to the above first embodiment.

Wavelength Tuning:

As mentioned, when the temperature of light source 7 changes, its spectrum varies. In addition to this, the emission intensity of the of light source 7 varies as well. This is illustrated in FIGS. 3-6.

Figure 3:
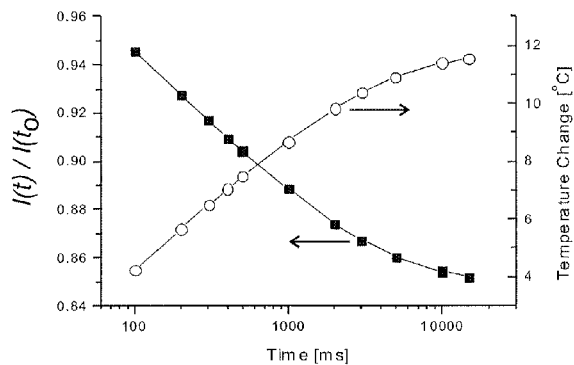
FIG. 3 shows the intensity change and corresponding change of temperature of a type A LED.
Figure 4:
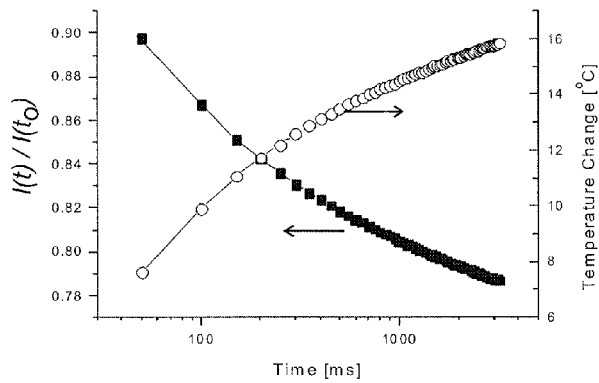
FIG. 4 shows the intensity change and corresponding change of temperature of a type B LED.

FIGS. 3 and 4 show the changes in intensity I(t) and temperature of type A and B LEDs with time t after switching them on with a current of 20 mA. I(0) designates the intensity at the initial stage at t=0. As can be seen, intensity decreases while temperature increases. This effect should be taken into account for improved signal accuracy, see below.

Figure 5:
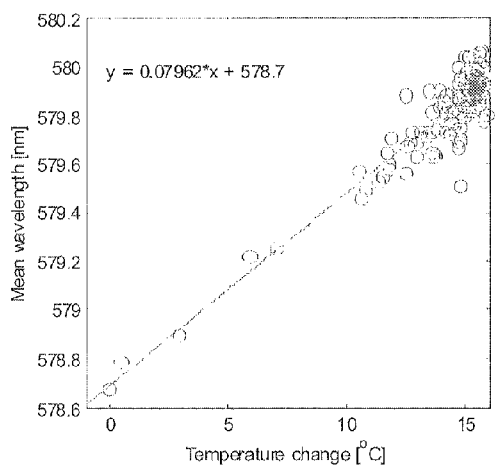
FIG. 5 shows the wavelength change as a function of temperature of a type B LED.
Figure 6:
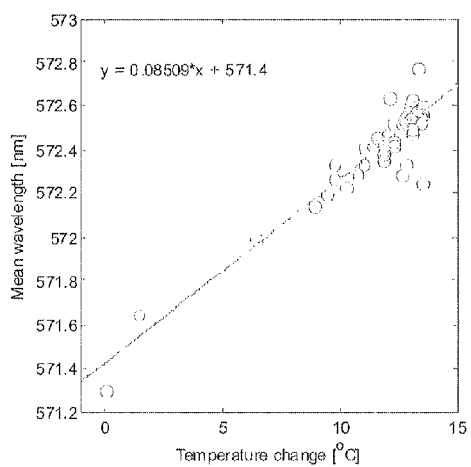
FIG. 6 shows the wavelength change as a function of temperature of a type A LED.

FIGS. 5 and 6 show the change of the mean wavelength of type A and B LEDs as a function of temperature. As can be seen, the wavelength shift is in the order of 1 nm for 10° C.

Figure 7:
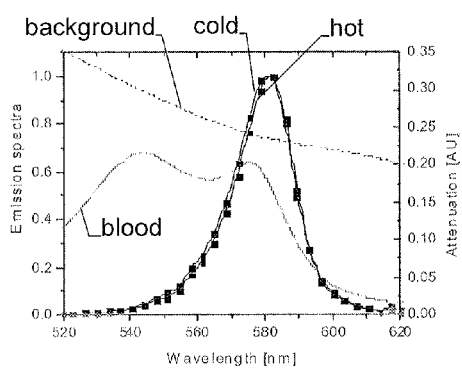
FIG. 7 shows the emission spectrum of a cold and a hot type A LED as well as the absorptivity of blood and background tissue.
Figure 8:
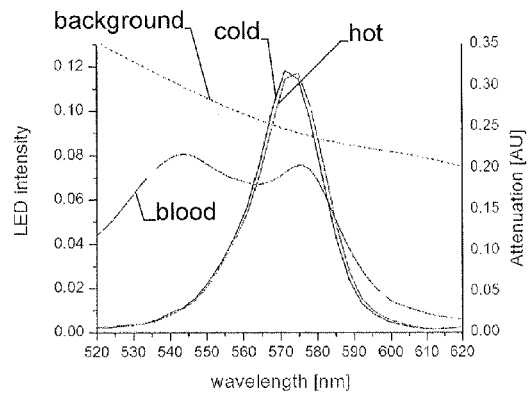
FIG. 8 shows the emission spectrum of a cold and a hot type B LED as well as the absorptivity of blood and background tissue.

FIGS. 7 and 8 show the emission spectra of type A LED (FIG. 7) and type B LED (FIG. 8) in cold and hot state, together with the absorption spectrum of blood as well as the absorption spectrum of the rest of the near-surface body tissue.

In order to accommodate for the temperature dependence of the intensity, the device can be calibrated as follows:

1. The device is brought into contact with a "white" non-absorbing diffuser having wavelength-independent scattering properties (in the spectral region of light source 7) similar to the scattering of body tissue. For example, such a diffuse can be a reflection standard made of Spectralon or Teflon. The diffuser is arranged such that light from light source 7 enters the diffuser and is scattered to arrive at light detector 8.

2. The current through the light source is switched on at a time 0.

3. At times $t_1, t_2, \ldots t_N$ with N>1 the signal $I_r(t_i)$ of light detector 8 is recorded. At least the first time $t_1$ should be shortly after time 0, in particular within 1 second or less after time 0, such that the temperature at time $t_1$ is not yet in its steady state (cf. FIGS. 3 and 4). This allows to determine a reference response $I_r(t)$ for at least some discrete times t or operating conditions (temperatures T) of the device. This reference response describes the behavior of the intensity signal of light detector 8 when operating the device on a body whose reflectivity from light source 7 to light detector 8 does not depend on the used wavelength of light source 7.

In more general terms, a reference signal Ir(T) is determined for each operating condition or temperature T to be used later. The reference signal Ir(T) corresponds to the intensity signal measured by light detector 8 if the light from light source 7 operating under the given operating condition T is reflected into said light detector by means of a body whose reflectivity does not depend on the wavelength of light source 7, i.e. whose spectral response is flat over the used wavelength range.

When the device is now brought into contact with living skin for measurements, the signal I(T) from light detector 8 (which has already been divided by correction factor $\alpha$ if a monitoring unit 19 as described above is used) is divided by the corresponding value of the white body response $I_r(T)$ at the same time or temperature T, and the inversed logarithm of the resulting quotient is a light attenuation A(T) according to eq. (2), at the given time or temperature.

For example, when switching on the light at a time 0 and measuring at the times $t_1, t_2, \ldots t_N$ with N>1, the attenuation or attenuation signal is given by $$A = -\ln \frac{I(t_i)}{I_r(t_i)} \quad (15)$$

This value describes the optical attenuation caused by the body tissue.

In this arrangement, factor $\alpha$ can be obtained by a monitoring unit 19 only once at some predefined stage of the source equilibration (e.g. before or after measurements of the main signal). Alternatively, it can be obtained for all time points $t_i$, i=1 . . . N, when the main signal is measured and in this way each of N intensity measurements is compensated separately.

The different times $t_i$ correspond to different temperatures $T_i$ of light source 7 and therefore to different states or wavelengths of the light source. In the following, we therefore also write $\lambda_i$ or $T_i$ instead of $t_i$ for designating the mean wavelength $\lambda_i$ or light source temperature $T_i$ at the time $t_i$.

Measuring Blood Perfusion:

a) Theory

As can be seen from FIGS. 7 and 8, the typical LED has a broad emission spectrum (compared to the changes of absorptivity of blood over wavelength), and the wavelength change caused by warming up can be relatively small, thus the overall change in the spectrum has to be analyzed using integration over the involved spectral range. If the LED emission at the time point t after switching-on is described by the power density $I_0^t(\lambda)$ where $\int I_0^t(\lambda)d\lambda = 1$, its attenuation can be written as follows (neglecting the spectral response function of the detector):

$$A(t) = \ln \int I_0^t(\lambda)\exp[-c l \varepsilon_{Hb}(\lambda)]\exp[-A_{bk}(\lambda)]d\lambda \quad (20)$$

We expect that the emission spectrum $I_0^{t1}(\lambda)$ immediately after switching on ("cold" state) and after the LED has warmed up $I_0^{tN}(\lambda)$ ("hot" state) are different, thus by comparing attenuation at these two states we can extract the wavelength-resolved information $$tPI = 4.342 \cdot [A(t_1) - A(t_2)] = \quad (21)$$

$$4.342 \cdot \ln \frac{\int I_0^{t1}(\lambda)\exp[-c l \varepsilon_{Hb}(\lambda)]\exp[-A_{bk}(\lambda)]d\lambda}{\int I_0^{tN}(\lambda)\exp[-c l \varepsilon_{Hb}(\lambda)]\exp[-A_{bk}(\lambda)]d\lambda}$$

wherein tPI is further referred as the "tuned perfusion index". The factor 4.342 was added to Eq. (21) for the conversion of the logarithm bases. As it will be clear to the skilled person, though, any other factor can be used as well.

tPI is a measure of the blood concentration c or, equivalently, of blood perfusion, just as the classic perfusion index PI of Eqs. (10) and (11).

Using the known absorption spectra of oxygenated and non-oxygenated hemoglobin as well as the emission spectra of the light sources, the value of tPI can be calculated from Eq. (21). The result of this calculation is shown in FIGS. 12 (type A LED) and 13 (type B LED).

Figures 14, 15:
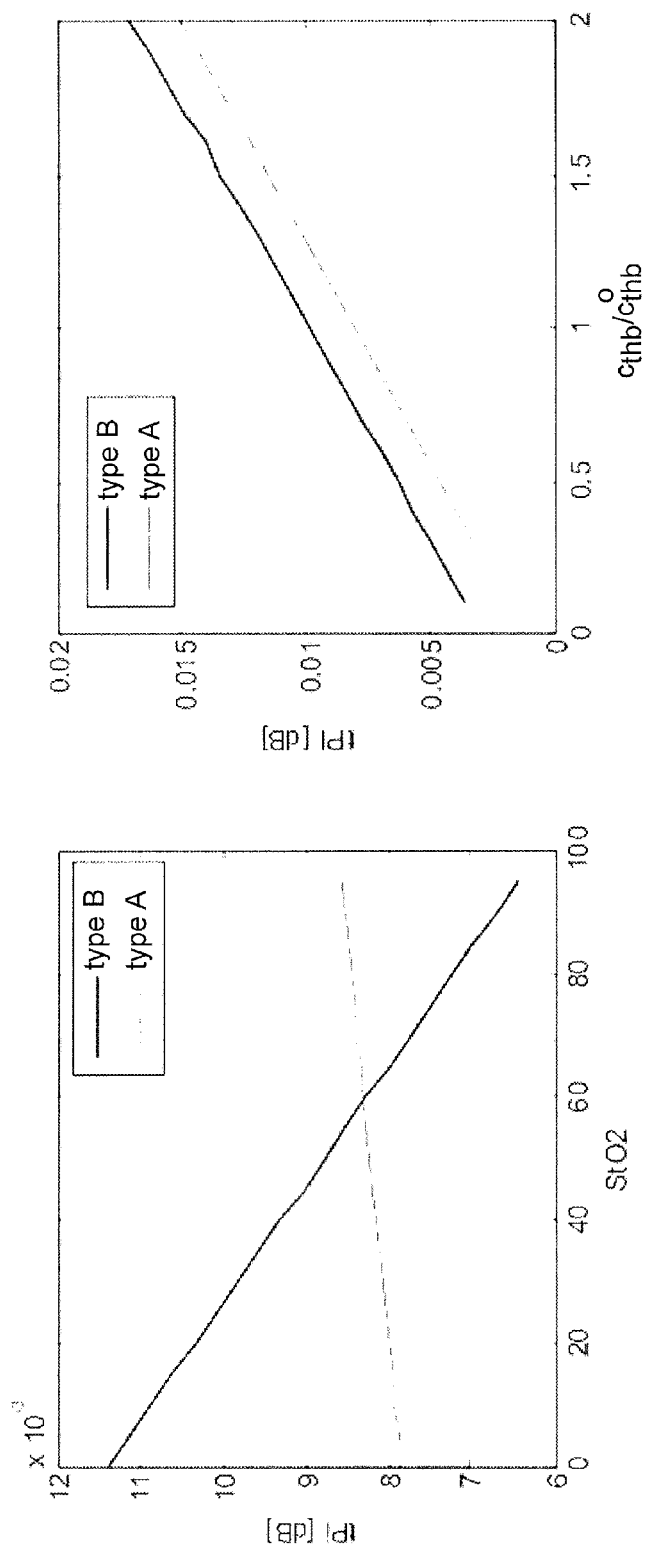
FIG. 14 shows tPI versus $StO_2$ from FIGS. 11 and 12 for type A and B LEDs.
FIG. 15 shows $c_{tHb}/c_{tHb}^0$ from FIGS. 11 and 12 for type A and B LEDs, where $c_{tHb}^0$ is a basal total haemoglobin concentration under normal physiological conditions.

FIG. 14 and FIG. 15 are sectional views of FIGS. 12 and 13, and they demonstrate the simulated response of the tPI to the changes in $StO_2$ and $c_{tHb}$ of type A and B LEDs. As it can be seen both LEDs have the similar sensitivity to the perfusion change, while the response of type B LED to oxygenation is significantly higher (FIG. 14).

b) Experiments

Figure 9:
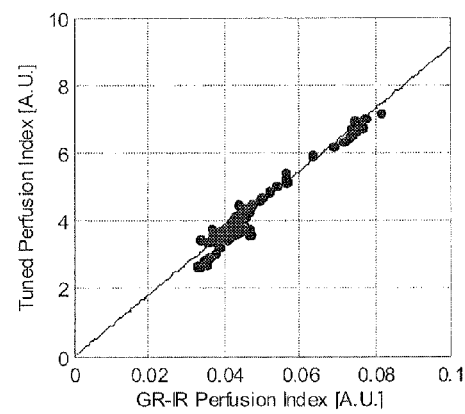
FIG. 9 shows the classical perfusion index versus the tuned perfusion index and a linear fit through the data.
Figure 10:
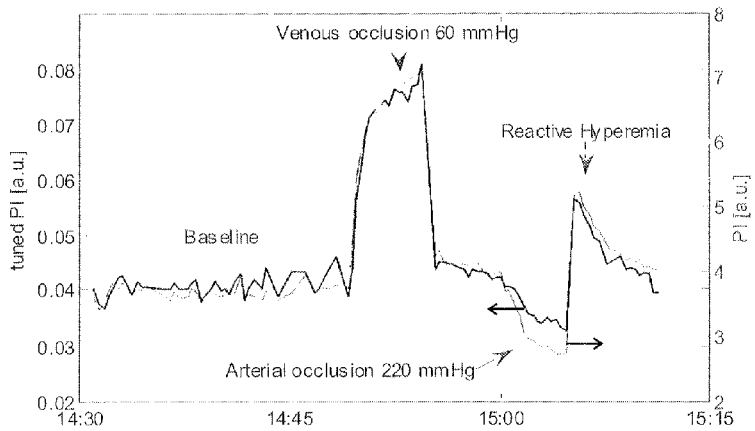
FIG. 10 shows the changes in the classical perfusion index (gray curve) and the tuned perfusion index (black curve) during a measurement.

In order to verify that tPI is a good replacement for the classically used perfusion index PI, a test measurement as shown in FIGS. 9 and 10 was carried out. The tests measurement was carried out with a classical detector having two LED light sources at 568 and 798 nm as well as with a device according to the present invention using a single LED operating at 578 nm (type A LED). The light source of the single LED device was operated by applying current pulses of 20 mA during 100 ms with current-less pauses of 50 ms between the pulses. The attenuation was measured by averaging during a first period between 0-50 ms and by averaging during a second period between 50-100 ms after start of each current pulse.

The experiment started at 14:30 with both devices as well as with an unpressurized cuff applied to the arm of a user. At 14:50 the cuff was pressurized to 60 mmHg in order to create venous but not arterial occlusion. At 14:55 the cuff was depressurized. Hence, an increased amount of venal blood was present at the time interval between 14:50 and 14:55. At 15:00 the cuff was pressurized to 220 mmHg, thereby creating venous and arterial occlusion. This caused blood oxygenation to drop. At 15:05 the cuff was depressurized, which caused reactive hyperemia in the tissue.

The gray curve in FIG. 10 shows the classic profusion index PI, while the black curve shows the tuned profusion index tPI. As can be seen, there is an excellent match between the two values until 15:00, which indicates that tPI is as good a measure of blood perfusion as PI. This is also illustrated in FIG. 9, which shows PI vs. tPI for the experiment of FIG. 10, showing the strong correlation between the two parameters.

FIGS. 9 and 10 show that wavelength tuning provides an efficient means for measuring blood perfusion.

Figure 11:
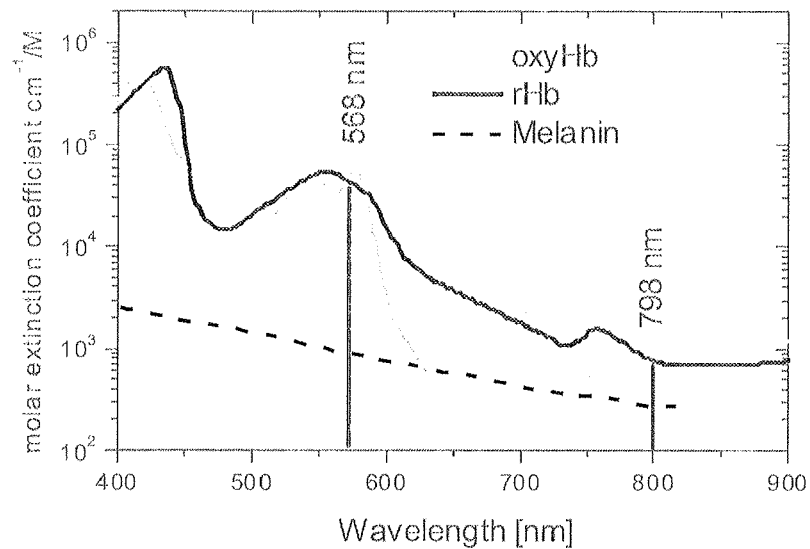
FIG. 11 shows the absorption spectra of oxyHb, rHb, and melanin.

The deviations of the curves at times after 15:00 are caused by the change of the absorption spectrum of blood as oxygenation changes. This is due to the fact that reduced hemoglobin and oxygenated hemoglobin have different absorption spectra, see FIG. 11.

tPI can be used to derive other parameters. For example, since blood perfusion and therefore WI varies with the heart beat rate, recording a time series of tPI or its underlying signals allows determining the heart beat rate.

c) Generalization

In general, in order to measure blood perfusion or any other parameter equivalent to blood perfusion or derived from blood perfusion, such as hemoglobin concentration per tissue volume or the heart beat rate, the following steps have to be carried out:

1) A light source and a light detector are placed in contact with the tissue in such a manner that the light detector measures the amount of light transmitted from the light source through the tissue to the light detector.

2) The light source is operated under a first condition where it has a first temperature, such as the operation of the light source at a time $t_1$ shortly after switching the light source on. A first signal, such as $A(t_1)$, is measured by means of the light detector.

3) The light source is operated under a second condition where it has a second temperature different from the first temperature, such as the operation of the light source at a time $t_2 > t_1$, and a second signal, such as $A(t_2)$, is measured by means of the light detector.

4) The at least two signals are combined in order to determine the parameter. This can e.g. occur by calculating the difference of the two signals, i.e. by calculating $A(t_1) - A(t_2)$ (or, equivalently, any value depending on this difference, such as a multiple of this difference, or any other mathematical function of this difference).

5) The result of step 4 can then be used to derive the desired parameter, such as blood perfusion, e.g. using calibration data stored in memory 16, such as a look-up table or a parameterized function.

The calibration data mentioned for step 5 can e.g. be obtained using calibration measurements, e.g. by measuring the desired parameter with a conventional reference method and by using multiple regression analysis for obtaining the calibration data. During the multiple regression, the attenuation signals $A(t_1)$, $A(t_2)$ are used as independent parameters, while the values of the parameter obtained by the reference method are used as a dependent variable. The model used during regression can be a simple linear model, albeit more elaborate models may be used as well.

In order to improve measurement accuracy, the skin temperature $T_S$ as measured by temperature sensor 13 can be used as a further input signal (and a further independent signal during regression). Similarly direct measurements of the light intensity emitted by the source (LED) can be performed with the dedicated monitoring detector, for example monitoring PiN diode, placed in the vicinity of the LED in order to collect the light directly from the LED without passing through the tissue.

If the desired parameter requires repetitive measurements (such as for determining the heart beat rate), above steps 2 to 4 are repeated, and the blood perfusion or the raw signals or their difference is recorded for each step 4, together with the time of the measurement. The time series generated in this manner is then analyzed for determining the desired parameter. The heart beat rate, for example, can be determined by calculating the distances between consecutive peaks in blood perfusion.

For increased accuracy, the light source can also be operated under N>2 conditions corresponding to further, different temperatures. At each condition, a signal A is measured by means of light detector 8. In particular, in pulsed operation of the light source, measurements can be carried out at N>2 times after switching the light source on. In that case there are more measurements than unknowns, which allows to further increase accuracy of the results. Again, multiple regression analysis can be used to determine the calibration data.

As mentioned, steps 2 to 4 can be repeated in order to sample the signals at the different phases of the heart or breath cycles and reduced the noise by averaging those measurements.

Measuring Blood Oxygenation:

a) Theory

If oxygenation of the blood has to be determined, two substances with unknown concentration are involved (oxyHb and rHb), which contribute to the blood attenuation $A_{Hb}=A_{oxyHb}+A_{rHb}$, and an unknown background attenuation $A_{bk}$. In this way the total attenuation is defined as follows $$A=A_{oxyHb}+A_{rHb}+A_{bk} \quad (30)$$

In order to find the three unknowns, one should measure at least at three wavelengths $\lambda_1$, $\lambda_2$, and $\lambda_3$. Using Eq. (2):

$$c_{oxyHb}\epsilon_{oxyHb}(\lambda_1)l+c_{rHb}\epsilon_{rHb}(\lambda_1)l+A_{bk}=A(\lambda_1)$$

$$c_{oxyHb}\epsilon_{oxyHb}(\lambda_2)l+c_{rHb}\epsilon_{rHb}(\lambda_2)l+A_{bk}=A(\lambda_2)$$

$$c_{oxyHb}\epsilon_{oxyHb}(\lambda_3)l+c_{rHb}\epsilon_{rHb}(\lambda_3)l+A_{bk}=A(\lambda_3) \quad (31)$$

Here we make an assumption that the path length l and background attenuation are wavelength independent—this corresponds to the assumption that the differences between the wavelengths $\lambda_1$, $\lambda_2$, and $\lambda_3$ are small. Eq. (31) form a linear system, which can be solved in respect to oxygenation and concentrations of oxyHb and rHb.

In practical applications, instead of using an accurate theoretical model, however, regression of a parameterized empirical or semi-empirical model can be used as well, e.g. multiple linear regression as described in the next section.

Figure 16:
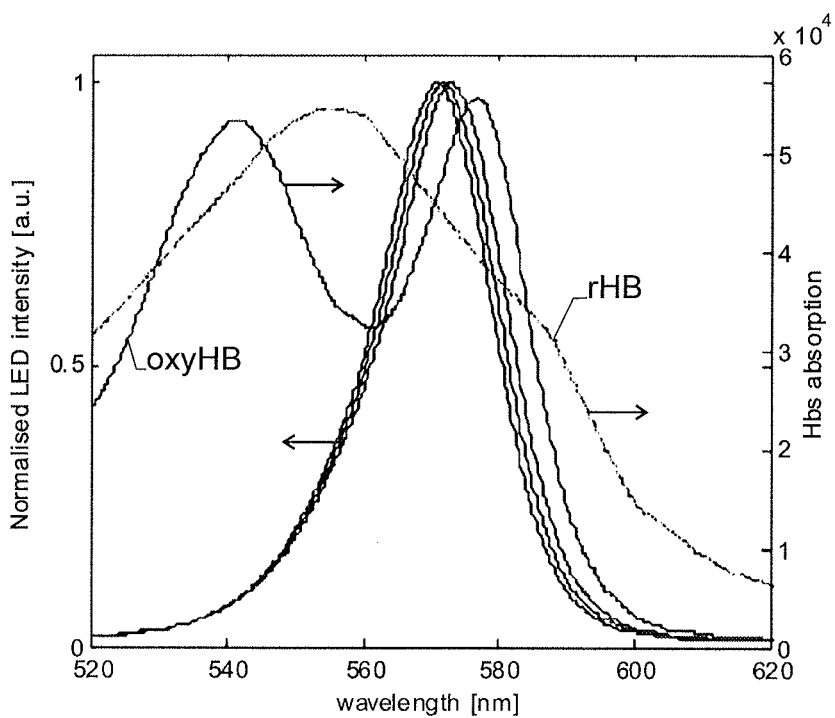
FIG. 16 shows the spectral tuning of a type B LED (leftmost line—cold state (initial state after switching on), middle line—an intermediate state, rightmost line—hot state), while the absorption spectra are those of oxyHb and rHb.

FIG. 16 depicts three spectra of a type B LED obtained at different stages of warming up. One can appreciate that, with the warming up of the LED and with the shift of the central wavelength towards the higher wavelengths, absorption of oxyHb is increasing, while absorption of rHb is decreasing. Due to the broad spectrum of the LED the exact changes of the absorption of the light is difficult to quantify. Therefore, the coefficients for the estimation of $StO_2$ from the measured attenuation signals $A(\lambda_1)$, $A(\lambda_2)$, $A(\lambda_3)$ can best be found by means of multiple regression analysis. For this purpose, calibration measurements are carried out, during which oxygenation-changing procedures are applied to the user while $A(\lambda_1)$, $A(\lambda_2)$, $A(\lambda_3)$ are measured together with the value of $StO_2$. For measuring the value of $StO_2$ a reference method is used. Multiple regression analysis can then be carried out for correlating the measured attenuation signals $A(\lambda_1)$, $A(\lambda_2)$, $A(\lambda_3)$ with $StO_2$.

Additionally, time-resolved measurements can be performed, with the measurement cycle repeated continuously. In this way the pulsation wave can be analyzed which allows to study the blood volume changes associated with the arterial blood. This approach is similar to the conventional photoplethysmography employing at least two light sources with distinctive wavelengths and allows to estimate the oxygenation of the arterial and venous blood separately.

b) Calibration

As a reference method, full-range optical reflection spectroscopy with a broad white light source can, for example, be used. In this case the measured spectrum can be fitted with the known spectra of skin chromophores and the corresponding concentration can be extracted. The $StO_2$ then can be easily calculated from the concentrations.

The device of the present invention is applied to an arm of the user for measuring the attenuation signals $A(\lambda_1)$, $A(\lambda_2)$, $A(\lambda_3)$. Close to this device, the fiber end of a spectrometer is applied to the user's arm for carrying out the reference measurements of $StO_2$. Further, a cuff is applied to the user's arm in order to generate arterial and venous occlusion of the arm as described in the following.

During calibration, an arterial occlusion is caused, followed by a venous occlusion. During an arterial occlusion the inflow of arterial blood and outflow of the venous blood are blocked, which results in the continuous reduction of the oxyHb content in the tissue. At the same time total blood volume (perfusion) might decrease or increase. After releasing the pressure, reactive hyperemia occurs, which leads to an increase of the blood amount, and of oxyHb in particular, which leads to elevated levels of $StO_2$.

During the venous occlusion only the venous outflow is impeded, which results in an accumulation of the rHb content and a decrease of the tissue oxygenation.

The experimental protocol consisted of the following steps with duration of approximately 4 minutes each:
1. equilibration stage
2. arterial occlusion
3. reactive hyperemia and equilibration
4. venous occlusion
5. equilibration stage The measurements were performed on the lower left arm, while the pressure cuff was fixed on the upper left arm.

The optical fibers for the reference spectroscopy were placed close to the device according to the invention in order to minimize effects of skin heterogeneity. Reference measurements were carried out in parallel with the measurements of the device.

Five experiments were performed in total on different points of the lower arm on different days in order to include variability of skin conditions.

Linear multiple regression analysis using the signals from the device as independent variables and $StO_2$ from the spectrometer as dependent variable was carried out.

In addition to the attenuation signals $A(\lambda_1)$, $A(\lambda_2)$, $A(\lambda_3)$, the skin temperature $T_S$ measured by the device was used as a fourth independent variable, and the negative logarithm the emitted intensity correction factor $\alpha$ measured by the monitoring device 19 was used as fifth independent variable.

Figure 17:
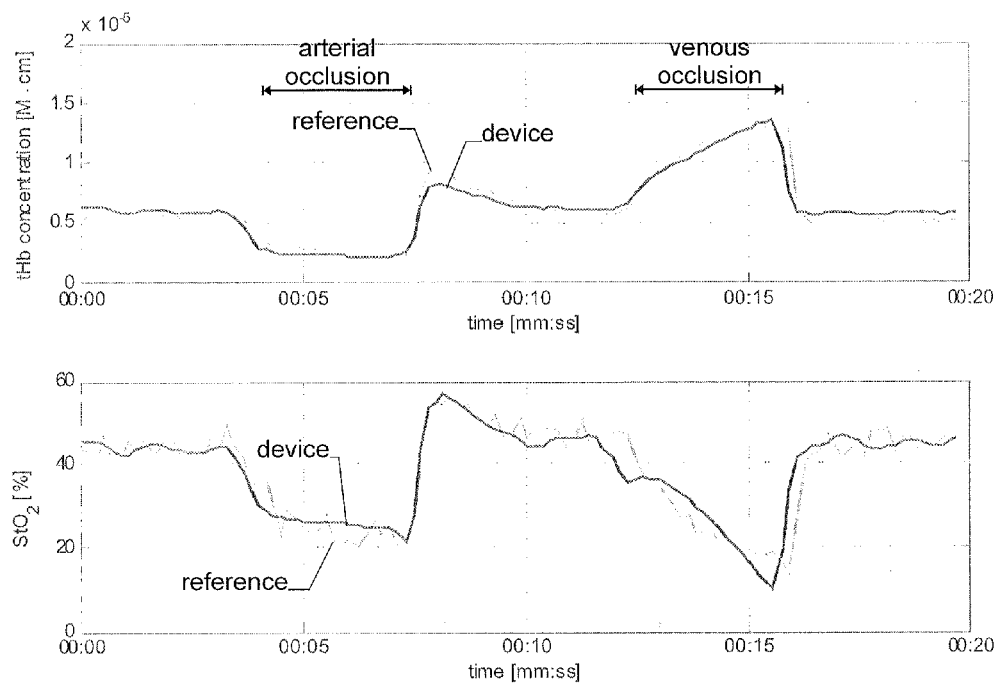
FIG. 17 is an illustration of $c_{tHb}$ (top graph) and $StO_2$ (bottom graph) fits with the data measured by the device for a single experiment.

FIG. 17 shows the result of this procedure for a single measurement cycle for the determination of $StO_2$ and tHb concentration, both by means of the reference method (gray line) and the device (black line). As can be seen, there is an excellent correspondence of the two signals.

Figure 18:
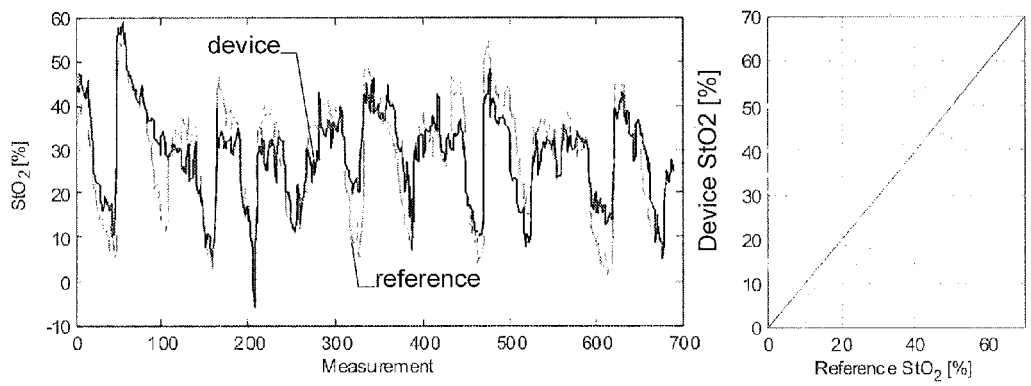
FIG. 18 shows the data merged from several oxygenation measurements (left plot): gray curve—reference data, black curve—results obtain with multiple regression fits using the data measured by the device; right plot shows the cross-plot of the same data.

We have observed high reproducibility of the reference $StO_2$ measurements from one experiment to another, which can be seen in the left graph of FIG. 18, where all the accumulated $StO_2$ data is merged into one continuous curve. The standard deviation of the total $StO_2$ change is 12.6%. The data obtained by means of the device of the present invention is represented in the same graph. The cross plot at the right of FIG. 18 shows the strong correlation between the reference signal and the measured signal.

Figures 19, 20:
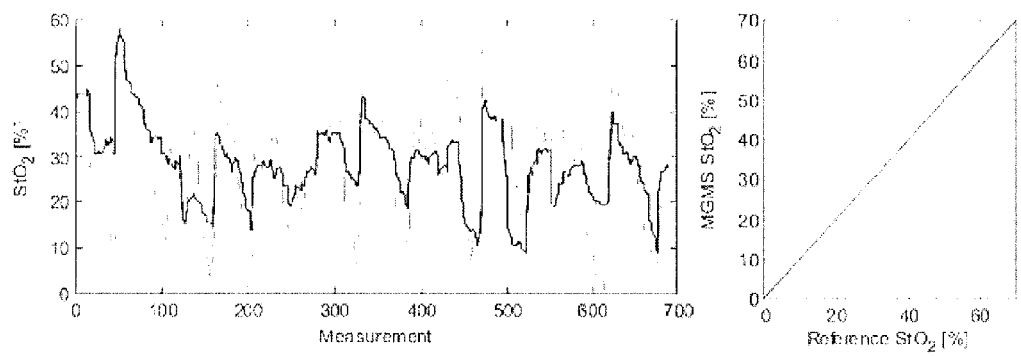
FIG. 19 shows a table of the fitting results underlying the regression used for FIG. 18.
FIG. 20 shows the data merged from several oxygenation measurements using three LEDs with different mean wavelengths: left plot, gray curve—reference data, black curve—results obtained with multiple regression fits using the data measured with the LEDs; right plot shows the cross-plot of the same data.

The fit parameters obtained by the multiple regression analysis are shown in FIG. 19. As one can see from the r-values in FIG. 19, the attenuations of the wavelengths $\lambda_1$, $\lambda_2$, $\lambda_3$ are the most important independent values in the model. In fact, if the model is reduced to only those three signals, the $R^2$ decreases only moderately to 0.602. The monitoring diode and skin temperature signals help to account for the variations of the outside temperature and the attachment of the sensor.

The signs of the coefficients for $A(\lambda_3)$ and $A(\lambda_1)$ suggest that a higher attenuation of the hot signal $A(\lambda_3)$ in respect to cold $A(\lambda_1)$ indicates higher oxygenation. This is in a full agreement with the discussion above.

To demonstrate the high quality of the results obtained by the present device, an alternative device having three differently colored LEDs (green, red and infrared) was used during the same experiments.

FIG. 20 presents the performance of the alternative device using signals from the green, red and infrared diodes, as well as skin temperature. The $R^2$ obtained by fitting the data of the alternative device is 0.468 (RMS error=9.2%), which is even smaller than for the present device using only the attenuations for hot, cold and reference conditions.

The fact that the present device has a higher predictive power for the tissue oxygenation than the alternative device proves that the proposed wavelength tuning is a technique well suited for measuring tissue parameters.

It should be noted that the red and infrared wavelengths often used in conventional clinical oximeters are not well suited for the reflectance oximetry, which is indicated by unsatisfactory performance of the alternative device using these signals. This may be due to the high range of the blood perfusion changes which is known to affect red-infrared oximetry.

In general, the discrepancy in the oxygenation estimation even with the best tunable model can be attributed to the non-uniformity of the perfusion and oxygen distribution in the arm and differences in the attachment of the reference fiber probe and the device. For example, different pressures of the reference probe and the device can lead to a different blood amount under both sensors, as well as to different oxygenation. Another reason for difference may be due to the different depths probed with device and reference probe, due to slight different source-detector distances.

Notes:

When measuring blood oxygenation or any other parameter indicative of the ratio between oxygenated and non-oxygenated hemoglobin, the measurement should be carried out in a spectral region where the absorption of rHb and oxyHb show very different wavelength dependence, in particular where the slopes of the absorption spectra of rHb and oxyHb have opposite signs. In that case, the influence of oxygenation on the measured attenuation signals $A(\lambda_1)$, $A(\lambda_2)$, $A(\lambda_3)$ is strongest. From FIG. 16 it can be seen that this is the case in the spectral ranges between 530 and 550 nm as well as between 560 and 580 nm. Hence, for that application, light source 7 should have a mean wavelength either between 530 and 550 nm or between 560 and 580 nm, and/or its spectral half-width should be not larger than approximately 20 nm, in particular not larger than 10 nm, if it emits light in the spectral range between 530 and 550 nm or not larger than approximately 20 nm, in particular not larger than 10 nm, if it emits light in the spectral range of 560 and 580 nm.

On the other hand, when measuring perfusion or any other parameter indicative of perfusion, but if the measured result should not be affected by blood oxygenation, the measurement should be carried out in a spectral region where rHb and oxyHb show absorptions having similar wavelength dependence, in particular in the neighborhood of the isosbestic points where the slopes of the absorption spectra of rHb and oxyHb are similar. In that case, the influence of oxygenation on the measured attenuation signals $A(\lambda_1)$, $A(\lambda_2)$, . . . is weakest. From FIG. 16 it can be seen that this is the case in the spectral ranges 520-540 nm and 580-600 nm.

The present device can be used for a large variety of applications. In addition to the applications mentioned so far, it can be used for hemodynamic monitoring, such as for monitoring the physical status of personnel of dangerous professions, deployed in high stress and extreme environments, e.g. rescue workers, firefighters or soldiers under battlefield conditions neonatal monitoring persons with a risk of anemia or hypoxia dialysis conditions sport and fitness applications.

Monitoring capabilities of the current approach are not limited to oxy- and reduced haemoglobins, but can be also applied to other forms of Hb, like fetal Hb, carboxyhemoglobin, carbaminohemoglobin, methemoglobin, myoglobin etc. However, the different wavelength region of measurements or additional light sources might be required to distinguish different forms of haemoglobin. These additional sources can also have the tuning capabilities or have a fixed wavelength.

In the embodiments above, a reflection measurement was carried out, with light source 7 and light detector 8 being arranged side by side over a surface of the tissue. Alternatively, the present invention can also be used in transmission mode, with light source 7 and light detector 8 being arranged on opposite sides of a body part, such as an ear lobe, and the light being transmitted through the body part.

While there are shown and described presently preferred embodiments of the invention, it is to be distinctly understood that the invention is not limited thereto but may be otherwise variously embodied and practiced within the scope of the following claims.

FURTHER REFERENCES

Nitzan, M. & Engelberg, S. Three-wavelength technique for the measurement of oxygen saturation in arterial blood and in venous blood. J Biomed Opt, Jerusalem College of Technology, Department of Applied Physics/Medical Engineering, P.O. Box 16031, Jerusalem, 91160 Israel., 2009, 14, 024046

M Osawa and S Niwa, A portable diffuse reflectance spectrophotometer for rapid and automatic measurement of tissue, 1993 Meas. Sci. Technol. 4 668-676

Diffey, B. L.; Oliver, R. J. & Farr, P. M. A portable instrument for quantifying erythema induced by ultraviolet radiation. Br J Dermatol, 1984, 111, 663-672

Y. P. Sinichkin, N Kollias, G I Zonios, S R Utz, V. V. Tuchin, Reflectance and fluorescence spectroscopy of human skin in vivo, 2002, Handbook of Optical Biomedical Diagnostics, pp. 727-785

J W Feather et al, A portable scanning reflectance spectrophotometer using visible wavelengths for the rapid measurement of skin pigments, 1989 Phys. Med. Biol. 34 807-820

H. Liu, D. A. Boas, Yu. Zhang, A. G. Yodh, and B. Chance, "Determination of optical properties and blood oxygenation in tissue using continuous NIR light," Phys. Med. Biol., Vol. 40, pp. 1983-1993 (1995).

Berardesca, E.; Elsner, P. & Maibach, H. I. (ed.) Bioengineering of the skin: cutaneous blood flow and erythema CRC Press, Roca Baton, USA, 1995

Serup, J.; Jemec, G. & Grove, G. L. (ed.) Handbook of Non-Invasive Methods and the Skin CRC Press, Boca Raton, USA, 2006

The invention claimed is:

1. A method for measuring at least one physiological parameter of tissue by means of a semiconductor light source and of a light detector, wherein said parameter affects concentration of blood constituents, in particular different forms of hemoglobin, said method comprising the steps of
   a) placing said light source and said light detector such that said light detector measures an amount of light transmitted from said light source through said tissue,
   b) operating said light source under a first condition where it has a first temperature, and determining a first light attenuation signal by means of said light detector,
   c) operating said light source under a second condition where it has a second temperature different from the first temperature, and determining a second light attenuation signal by means of said light detector,
   d) determining said parameter using said first light attenuation signal and said second light attenuation signal,
   wherein said method further comprises the step of varying a current through said light source in order to create said different operating conditions by switching said current from a first level to a second, different level and determining at least part of said attenuation signals at different times after switching said current while said light source has not yet reached thermal equilibrium.

2. The method of claim 1 wherein at least part of said attenuation signals are determined within 1 second from switching said current, in particular within 100 milliseconds.

3. The method of claim 1 further comprising the step of determining said parameter by calculating a difference between the first and the second light attenuation signals and/or the step of deriving said parameter from said attenuation signals using calibration data.

4. The method of claim 1 wherein said parameter is blood perfusion or any parameter depending on blood perfusion.

5. The method of claim 1 wherein said steps b) and c) are repeated for recording a time series of data, wherein a heart beat rate is derived from said time series of data.

6. The method of claim 1 comprising the step of operating said light source under N conditions where it has N different temperatures and measuring an attenuation signal at each condition, wherein N>2.

7. The method of claim 1 wherein for each operating condition said attenuation signal is determined by measuring an intensity signal by means of said light detector and dividing said intensity signal by a reference signal ($P_r$), wherein the reference signal ($P_r$) corresponds to an intensity signal measured by said light detector if the light from said light source operating under said operating condition is reflected into said light detector by means of a body whose reflectivity does not depend on the wavelength of said light source.

8. The method of claim 1 wherein said parameter is determined using said attenuation signals and calibration data, wherein said calibration data was obtained in a calibration procedure, which calibration procedure comprises the steps of
   performing a series of calibration measurements for different states of said tissue and, for each calibration measurement, recording said attenuation signals by means of said light detector and recording a value of said parameter by means of a reference method,
   using multiple regression for determining said calibration data with the recorded attenuation signals being independent variables and the recorded values of said parameter being a dependent variable.

9. The method of claim 8 further comprising the step of using said skin temperature ($T_S$) as an independent variable during said multiple regression.

10. The method of claim 8 further comprising the step of using said attenuation signals as an independent variable during said multiple regression.

11. The method of claim 1 further comprising the step of measuring a skin temperature ($T_S$) of said tissue and using said skin temperature ($T_S$) for determining said parameter.

12. The method of claim 1 further comprising the step of monitoring light intensity signal emitted by the light source, in particular by means of a temperature sensor or light sensor, and scaling a signal from said light sensor by means of said monitored light intensity signal ($\alpha$).

13. The method of claim 1 wherein said parameter is indicative of a ratio between oxygenated and non-oxygenated hemoglobin in said tissue.

14. The method of claim 1 wherein said light source has a mean wavelength between 530 and 550 nm or between 560 and 580 nm, and/or wherein said light source emits
   between 530 and 550 nm and has a spectral half-width not larger than 20 nm, in particular not larger than 10 nm, or
   between 560 and 580 nm and has a spectral half-width not larger than 20 nm, in particular not larger than 10 nm.

15. The method of claim 1, wherein said light source has a mean wavelength between 520 and 540 nm or between 580 and 600 nm.

16. The method of claim 1 wherein said light source is a LED or a laser diode.

17. A device for measuring in-vivo at least one physiological parameter of tissue comprising
   a housing configured to be placed against said tissue,
   a semiconductor light source arranged in said housing,
   a light detector positioned to measure light transmitted from said light source transmitted through said tissue,
   a control unit for
   operating said light source under a first condition where it has a first temperature, and determining a first attenuation signal by means of said light detector,
   operating said light source under a second condition where it has a second temperature different from the first temperature, and determining a second attenuation signal by means of said light detector,
   determining said parameter using said first signal and said second attenuation signal, wherein said device is adapted to vary a current through said light source in order to create said different operating conditions by switching said current from a first level to a second, different level and determining at least part of said attenuation signals at different times after switching said current while said light source has not yet reached thermal equilibrium.

18. The device of claim 17 wherein said device is adapted to carry out the method of claim 1.

* * * * *